(12) United States Patent
Wodajo

(10) Patent No.: US 11,523,851 B2
(45) Date of Patent: Dec. 13, 2022

(54) EXPANDABLE OSSEOINTEGRATION BONE FIXATION APPARATUS FOR USE IN A VARIETY OF SETTINGS

(71) Applicant: Felasfa Wodajo, Potomac, MD (US)

(72) Inventor: Felasfa Wodajo, Potomac, MD (US)

(*) Notice: Subject to any disclaimer, the term of this patent is extended or adjusted under 35 U.S.C. 154(b) by 146 days.

(21) Appl. No.: 16/700,297

(22) Filed: Dec. 2, 2019

(65) Prior Publication Data

US 2020/0129212 A1 Apr. 30, 2020

Related U.S. Application Data

(63) Continuation of application No. 15/632,668, filed on Jun. 26, 2017, now Pat. No. 10,492,839.

(60) Provisional application No. 62/492,270, filed on Apr. 30, 2017.

(51) Int. Cl.
| | |
|---|---|
| A61B 17/72 | (2006.01) |
| A61F 2/46 | (2006.01) |
| A61F 2/00 | (2006.01) |
| A61B 17/80 | (2006.01) |
| A61F 2/28 | (2006.01) |
| A61F 2/30 | (2006.01) |
| A61B 17/68 | (2006.01) |

(52) U.S. Cl.
CPC ...... *A61B 17/7225* (2013.01); *A61B 17/8004* (2013.01); *A61F 2/0077* (2013.01); *A61F 2/28* (2013.01); *A61F 2/30* (2013.01); *A61F 2/4601* (2013.01); *A61B 17/683* (2013.01); *A61B 17/7233* (2013.01); *A61B 17/7241* (2013.01); *A61B 17/7258* (2013.01); *A61B 17/80* (2013.01); *A61F 2002/285* (2013.01); *A61F 2002/2817* (2013.01); *A61F 2002/30405* (2013.01); *A61F 2002/30507* (2013.01); *A61F 2002/30553* (2013.01); *A61F 2002/30579* (2013.01); *A61F 2310/00011* (2013.01)

(58) Field of Classification Search
CPC .......................................... A61B 17/72–7291
See application file for complete search history.

(56) References Cited

U.S. PATENT DOCUMENTS

| | | | | |
|---|---|---|---|---|
| 4,091,806 A | * | 5/1978 | Aginsky | A61B 17/7225 606/63 |
| 4,590,930 A | * | 5/1986 | Kurth | A61B 17/7258 606/63 |

(Continued)

*Primary Examiner* — Eduardo C Robert
*Assistant Examiner* — Steven J Cotroneo
(74) *Attorney, Agent, or Firm* — Charney IP Law LLC

(57) ABSTRACT

A cortical shaft bone fixation apparatus includes a housing having a leading portion and a trailing portion, the leading portion configured to fit within a diameter of an affected cortical shaft bone, the leading portion having first and second sections. The apparatus further includes an expansion mechanism adapted to transition the first and second sections from a first position to a second position, the first and second sections providing an outward force against the inside surface of the cortical shaft bone when the first and second sections transition from the first position to the second position, the trailing portion of the housing abutting a leading end of the affected cortical shaft bone. The trailing portion of the housing includes a pair of angled tapers extending inwardly toward each other to a minimum separation distance at an extreme end of the housing.

14 Claims, 5 Drawing Sheets

(56) References Cited

U.S. PATENT DOCUMENTS

| | | | | |
|---|---|---|---|---|
| 4,605,350 A | * | 8/1986 | Chater | F16B 13/0891 |
| | | | | 411/75 |
| 5,032,133 A | * | 7/1991 | Carbone | A61F 2/3662 |
| | | | | 623/23.26 |
| 5,116,378 A | * | 5/1992 | Carbone | A61B 17/7258 |
| | | | | 623/23.26 |
| 5,167,666 A | * | 12/1992 | Mattheck | A61F 2/36 |
| | | | | 623/23.27 |
| 5,554,191 A | * | 9/1996 | Lahille | A61F 2/447 |
| | | | | 606/247 |
| 5,653,763 A | * | 8/1997 | Errico | A61F 2/446 |
| | | | | 623/17.11 |
| 7,703,727 B2 | * | 4/2010 | Selness | A47B 91/028 |
| | | | | 248/188.2 |
| 7,799,081 B2 | * | 9/2010 | McKinley | A61F 2/4611 |
| | | | | 623/17.16 |
| 9,314,349 B2 | * | 4/2016 | Greenhalgh | A61F 2/4611 |
| 2003/0065396 A1 | * | 4/2003 | Michelson | A61F 2/4611 |
| | | | | 623/17.15 |
| 2004/0010313 A1 | * | 1/2004 | Aston | A61L 27/56 |
| | | | | 623/23.72 |
| 2009/0248024 A1 | * | 10/2009 | Edwards | A61B 17/7225 |
| | | | | 606/62 |

* cited by examiner

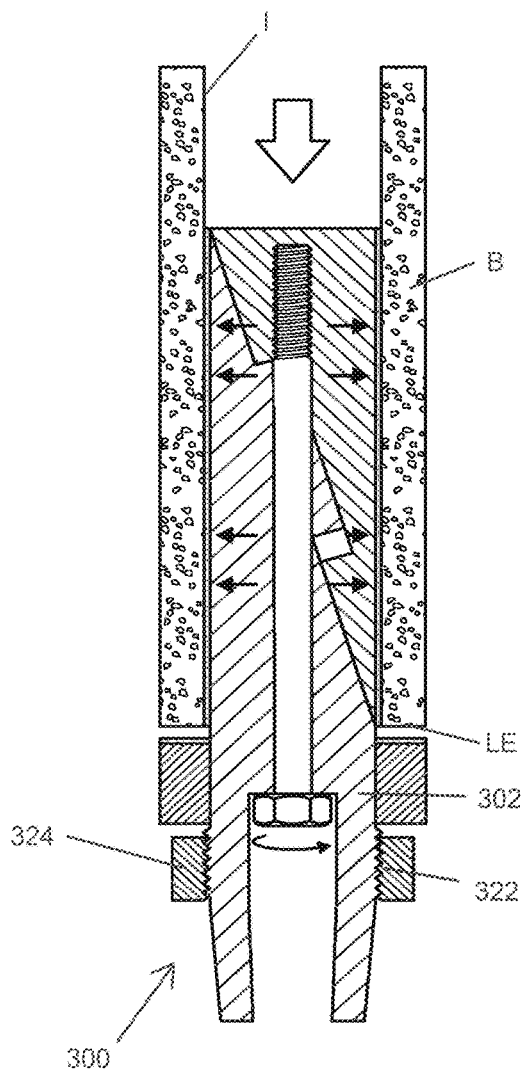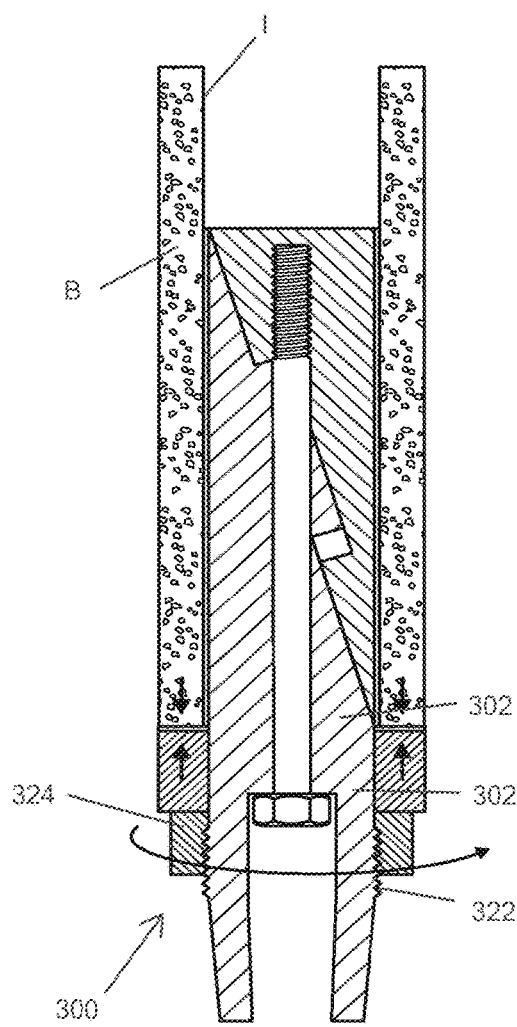
*FIG. 3A*  *FIG. 3B*

EXPANDABLE OSSEOINTEGRATION BONE FIXATION APPARATUS FOR USE IN A VARIETY OF SETTINGS

CROSS-REFERENCE TO RELATED APPLICATIONS

This application is a continuation application of U.S. patent application Ser. No. 15/632,668 filed on Jun. 26, 2017 titled "Expandable Osseointegration Bone Fixation Apparatus For Use In A Variety Of Settings," which claims the benefit of provisional patent application No. 62/492,270 filed on Apr. 30, 2017 titled "Expandable Osseointegration Bone Fixation Device" by the present inventor.

FIELD

The present embodiment relates to a bone fixation apparatus, and, in particular, to an intramedullary fixation apparatus configured to be durably affixed to an affected bone and enable osseointegration within a plurality of microscopic pores.

BACKGROUND

It is often necessary in orthopedic surgery to affix a metal device into the patient's bone. Typically, surgery such as bone fracture repair uses bone screws to attach metal plates to the bone in order to restrict movement and to ensure the correct positioning of the bones being repaired. However, in other scenarios, the metal device is intended to permanently be incorporated into the patient's skeleton. A common situation is hip or knee joint replacement where the implant is intended to durably adhere to the patient's bones.

Some clinical scenarios, such as patients who have had multiple revision surgeries or bone tumor resections are challenging for current devices, in particular when there is a short segment of bone or only cortical bone is available. In these cases, current fixation technologies provide less than optimal long-term fixation.

Furthermore, currently available devices which are intended for fixation into cortical (shaft) bone require manual impaction of the device to produce pressure between the device and the host bone, which is challenging to reliably reproduce and thus introduces the potential for surgical error. Other devices use a spring-loaded mechanism to produce compression between metal and only the leading edge of the bone. Thus, the osseointegration surface is limited to a small area and so patients are prohibited from bearing weight for many weeks, and even then, the risk of early failure remains high.

This invention is intended to take advantage of the natural tendency of bone to grow into porous metallic surfaces and develop a durable attachment via "osseointegration". This occurs when bone progenitor cells migrate into the metallic pores and form bone within and about the porous structure. This process is well known to allow for durable fixation of metal implants onto bone. Within the scope of the present invention, in each of the below embodiments, the porous and non-porous portions of the device may be coated with proteins from synthetic or animal source such as antibiotics, or include other coatings or radioactive materials to augment the therapeutic options of the invention.

SUMMARY OF THE INVENTION

Embodiments described herein include an expandable osseointegration bone fixation apparatus 100 for use in a variety of settings including orthopedic, craniomaxillofacial and veterinary applications. The apparatus 100 is configured to be affixed to a segment of bone B and allow osseointegration with the affected bone segment. The apparatus is designed to be compressed against both the inside I and the leading edge LE of an affected bone. The apparatus 100 includes a housing 102 containing an insert 104 further comprised of two diametrically opposed congruent sections 106, 108. An expansion bolt 110 at the centerline axis CL produces a sliding motion between the two sections 106, 108 and leads to incremental transition between a first contracted and a second expanded position. The housing 102 includes a first side 112 opposite a second side 114 whose diameters when added together are proportionate to the diameter of the affected bone B. The housing 102 is composed of a metallic material and designed to contain the insert 104 having the two diametrically opposed congruent sections 106, 108 at a trailing end 116 and a set of angled tapers 118 at the leading end 120. The apparatus 102 is compressed against the affected bone B by twisting the expansion bolt 110 causing horizontal expansion of the housing 102 while simultaneously advancing the tapers 118 further into the affected bone. Once inserted, a plurality of microscopic pores along the leading end 120 of the housing 102 and along the outer aspect of the tapers 118 enable osseointegration between the bone B and the several metallic surfaces of the apparatus 100.

In an alternative embodiment, the apparatus 200, 300 includes a plurality of grooves 222, 322 along the exterior walls of the housing portion 202, 302 outside the bone B which enables incremental tightening of a threaded collar 224, 324, causing compression between the collar and the leading edge LE of the bone, in addition to the interior I of the bone.

In a further alternative embodiment, the apparatus includes a collar with a porous surface to slide toward to the affected bone without rotation. An adjustable nut is then applied opposite the sliding collar. When this nut is tightened, it causes increased pressure between the collar and bone, in addition to the pressure between the outside surface of the tapers and the affected bone.

In a further alternative embodiment intended for use near the ends of bones, the apparatus includes a transverse bolt designed to cause expansion of the inserts in a direction perpendicular to longitudinal axis of the bone and a plurality of screws inserted at the leading end of the insert to increase coronal compression of the apparatus against the leading edge of the bone.

BRIEF DESCRIPTION OF THE DRAWINGS

A more complete understanding of the present invention, and the attendant advantages and features thereof, will be more readily understood by reference to the following detailed description when considered in conjunction with the accompanying drawings wherein:

FIG. 3A is a further alternate embodiment of the apparatus with a threaded nut to be used to compress a collar against bone;

FIG. 3B is a further alternate embodiment now with threaded nut turned to compress collar against bone;

Figure 1A:
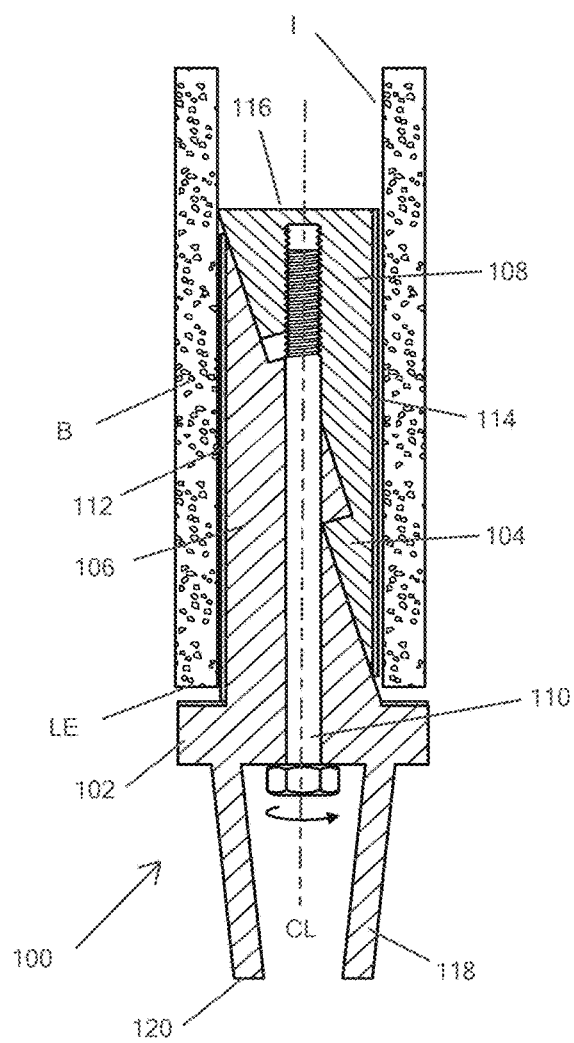
FIG. 1A is a perspective view of an expandable osseointegration bone fixation apparatus, with a tapered conical portion comprising the portion of the housing outside the bone, used to removably attach the apparatus to other metallic components.
Figure 1B:
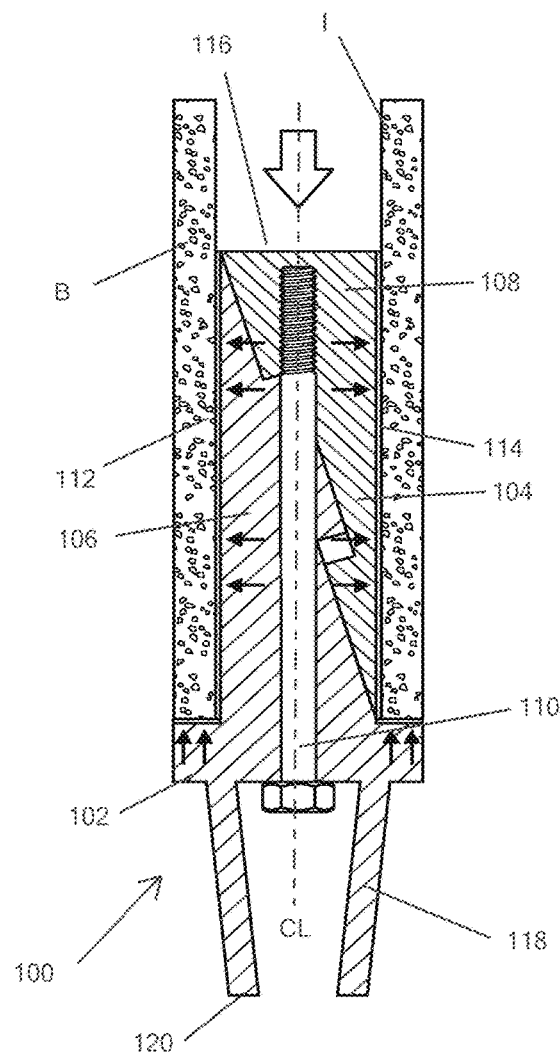
FIG. 1B is a view of the apparatus sliding between the contracted and expanded positions.
Figure 2A:
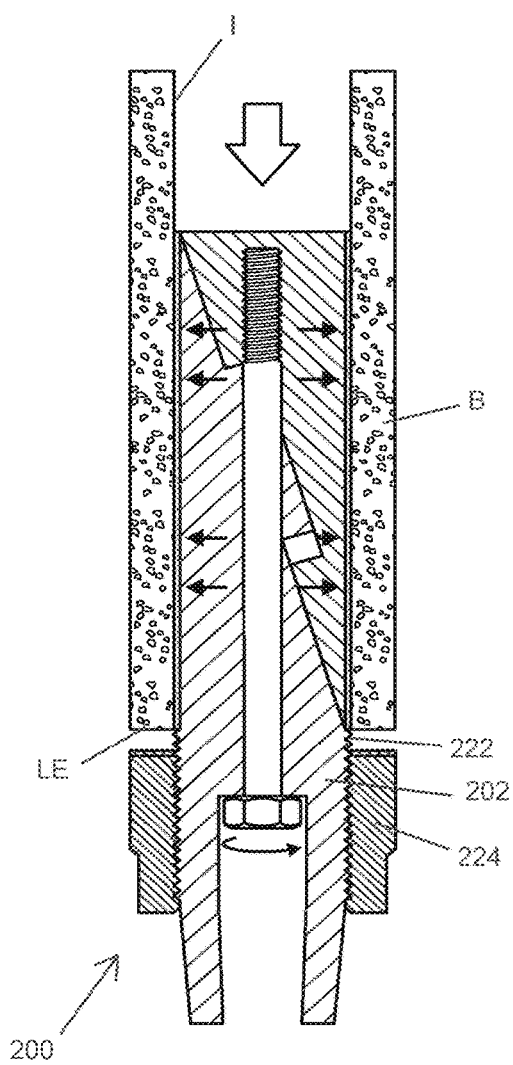
FIG. 2A is an alternate view of the apparatus in an expanded position and further including a threaded collar for additional compression at the end of the bone.
Figure 2B:
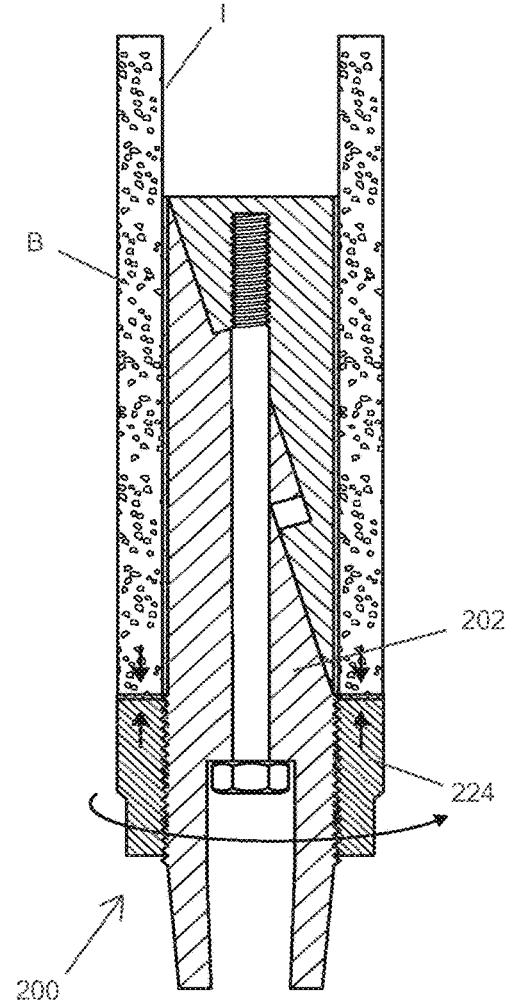
FIG. 2B is the alternate view of apparatus with the threaded collar now compressed against the bone.
Figure 4:
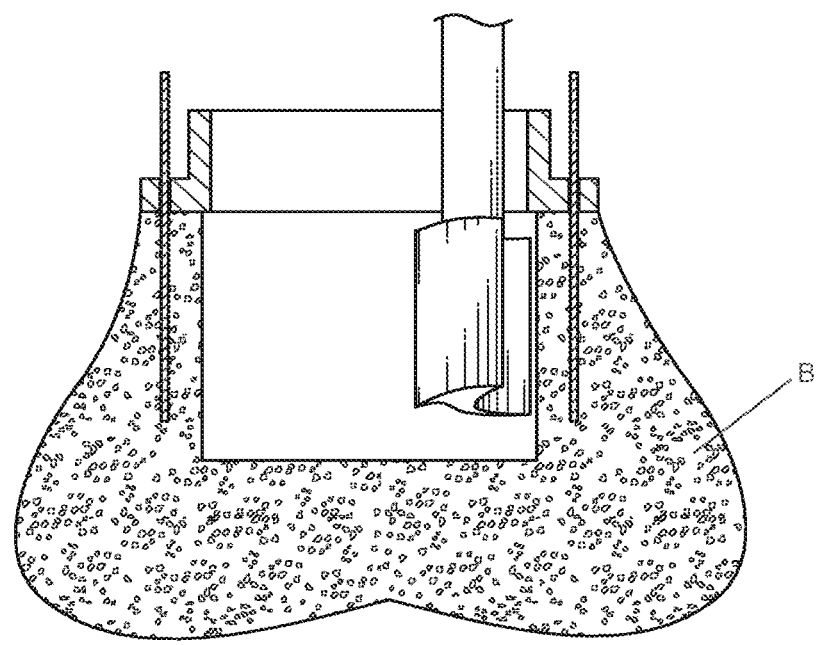
FIG. 4 is a further alternate embodiment of the apparatus intended for use near the end of a bone (metaphysis), demonstrating initial preparation of bone with router and guide.
Figure 5A:
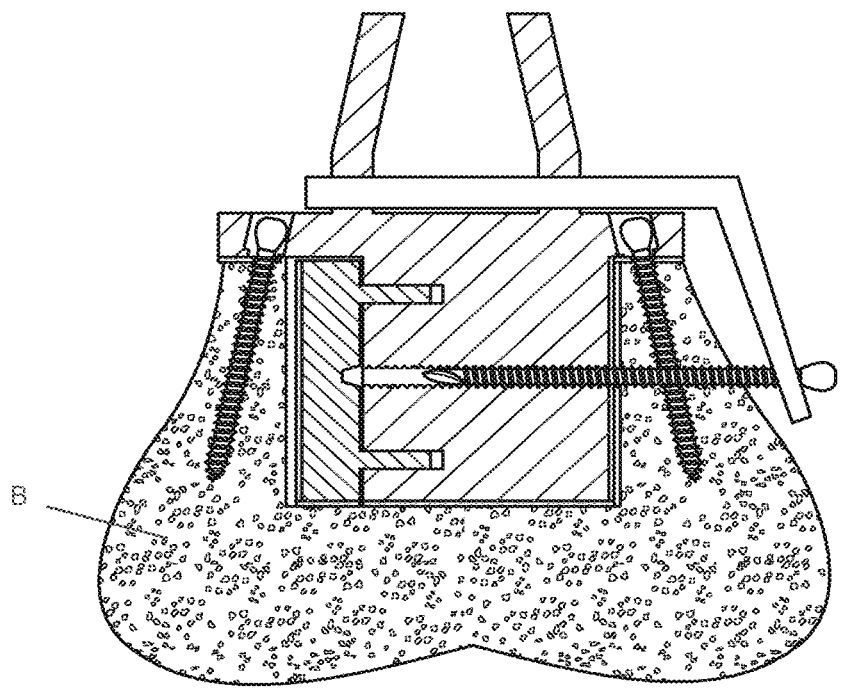
FIG. 5A is the alternate embodiment of the apparatus inserted into the bone, fixed with screws into the bone, internal transverse bolt placed using removable jig.
Figure 5B:
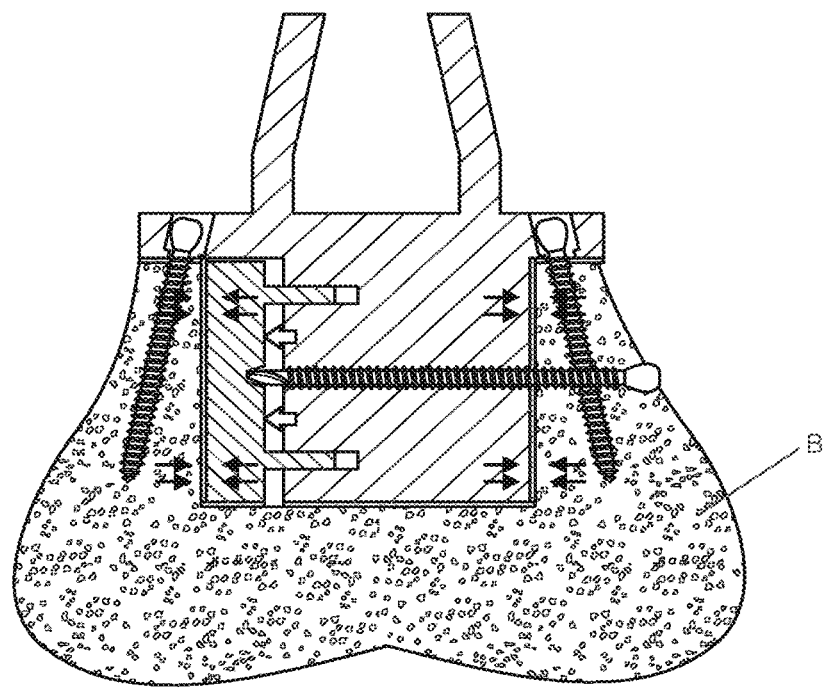
FIG. 5B is the alternate view of the apparatus now with the transverse bolt tightened, causing expansion of the device within the bone.

I claim:

1. An expandable osseointegration cortical shaft bone fixation apparatus, said apparatus comprising:
    a first section and a second section, said first section partially overlapping said second section, said first section including a first section inside surface abutting said second section and a first section outside surface opposite said first section inside surface;
    an insert mechanism configured to be in mechanical connection with said first section when inserted into the affected cortical shaft bone, said insert mechanism being adapted to cause said first section to move with respect to said second section upon rotation of said insert mechanism, forcing said first section outside surface against an inside of the affected cortical shaft bore;
    an external compression member adapted to move relative to said second section to be forced against a leading edge exterior surface of the affected cortical shaft bone;
    wherein said apparatus further comprises a connection member for connection to additional surgical components, said connection member comprising a pair of angled tapers, said angled tapers extending inwardly toward each other to a minimum separation distance at an extreme end of said apparatus, wherein said connection member is a cylindrical connection member.

2. The apparatus of claim 1, wherein the first and second sections enable lateral movement in a direction perpendicular to a centerline of said insert mechanism providing circumferential compression between said outside surface of said first section and the inside of the affected cortical shaft bone.

3. The apparatus of claim 2, wherein the first section and the second section are coated with a material having therapeutic properties.

4. The apparatus of claim 2, wherein the first and second sections are comprised of a metallic material having a portion including plurality of microscopic apertures to enable bone progenitor cells to migrate into the plurality of apertures and promote osseointegration.

5. The apparatus of claim 2, wherein an apparatus width is defined by an inside diameter of the affected cortical shaft bone.

6. The apparatus of claim 1, wherein the external compression member includes a planar portion forced against a leading edge exterior surface of the affected cortical shaft bone.

7. An expandable osseointegration bone fixation apparatus, comprising:
    a cylindrically shaped insert having proximal and distal ends, said insert having a first side with a first angled surface op site a second side with a second angled surface, said first side being at said distal end and said second side being at said proximal end;
    an insert mechanism adapted to be rotated to advance said cylindrically shaped insert against an inside surface of an affected cortical shaft hone; and,
    an external compression member adapted to apply a compressive force against a leading edge of the affected bone at said proximal end by being moveable relative to said second side;
    the apparatus further comprising a connection member for connection to additional surgical components, the connection member comprising a pair of angled tapers extending inwardly toward each other to a minimum separation distance at an extreme end of said apparatus, wherein said connection member is a cylindrical connection member.

8. The apparatus of claim 7, wherein said insert member may be rotated independent of advancement of said insert mechanism.

9. The apparatus of claim 7, wherein advancement of said insert mechanism may be achieved independent of rotation of said insert member.

10. The apparatus of claim 7, wherein said cylindrically shaped insert includes a plurality of microscopic pores to allow progenitor cell migration within the plurality of microscopic pores and promote osseointegration.

11. The apparatus of claim 7, wherein the external compression member includes a planar portion adapted to apply a compressive force against a leading edge of the affected bone.

12. A cortical shaft bone fixation apparatus with a porous surface for use in a variety of settings to promote osseointegration, comprising:
    proximal and distal ends;
    a first portion at said distal end and a second portion at said proximal end, said first portion and said second portion configured to partially fit within an internal diameter of an affected cortical shaft bone;
    a threaded insert mechanism adapted to move in a manner so as to provide an outward force between the apparatus and an inside surface of the affected cortical shaft hone when said first and second portions incrementally transition from a first position to an expanded second position;
    the apparatus further comprising an external portion at said proximal end, said external portion capable of moving independent of said first portion and said second portion to abut a leading end of the affected cortical shaft bone and to provide a force thereon;
    the apparatus further comprising a connection member for connection to additional surgical components, the connection member comprising a pair of angled tapers extending inwardly toward each other to a minimum separation distance at an extreme proximal end of said apparatus; wherein said connection member is a cylindrical connection member.

13. The apparatus of claim 12, wherein said connection member extends in a direction along a centerline axis of said apparatus.

14. The apparatus of claim 12, wherein a section of said external portion adapted to abut the leading end of the affected cortical shaft hone and to provide a force thereon is planar.

* * * * *